(12) United States Patent
Trautman et al.

(10) Patent No.: US 7,131,960 B2
(45) Date of Patent: Nov. 7, 2006

(54) APPARATUS AND METHOD FOR PIERCING SKIN WITH MICROPROTRUSIONS

(75) Inventors: Joseph C. Trautman, Sunnyvale, CA (US); Richard L. Keenan, Saratoga, CA (US); Ahmad P. Samiee, Sunnyvale, CA (US); WeiQi Lin, Palo Alto, CA (US); Michel J. N. Cormier, Mountain View, CA (US); James A. Matriano, Mountain View, CA (US); Peter E. Daddona, Menlo Park, CA (US)

(73) Assignee: Alza Corporation, Mountain View, CA (US)

(*) Notice: Subject to any disclaimer, the term of this patent is extended or adjusted under 35 U.S.C. 154(b) by 183 days.

(21) Appl. No.: 09/976,798

(22) Filed: Oct. 12, 2001

(65) Prior Publication Data

US 2002/0123675 A1    Sep. 5, 2002

(51) Int. Cl.
*A61B 17/20*    (2006.01)

(52) U.S. Cl. .......................... 604/46; 604/48; 604/500; 604/173

(58) Field of Classification Search ............. 604/890.1, 604/20, 506, 46, 500, 19, 21, 501, 130, 136, 604/137–139, 144, 156, 157; 600/309, 316, 600/322, 325, 327–328, 332, 334, 341, 344; 606/181, 183, 184–189
See application file for complete search history.

(56) References Cited

U.S. PATENT DOCUMENTS

| | | | |
|---|---|---|---|
| RE25,637 E | 9/1964 | Kravitz et al. | 128/253 |
| 3,814,097 A | 6/1974 | Ganderton et al. | 128/268 |
| 3,964,482 A * | 6/1976 | Gerstel et al. | 604/890.1 |
| 5,250,023 A | 10/1993 | Lee et al. | 604/20 |
| 5,279,544 A * | 1/1994 | Gross et al. | 604/20 |
| 5,879,326 A * | 3/1999 | Godshall et al. | 604/506 |
| 6,048,337 A | 4/2000 | Svedman | |
| 6,364,889 B1 * | 4/2002 | Kheiri et al. | 606/181 |

FOREIGN PATENT DOCUMENTS

| | | | |
|---|---|---|---|
| GB | WO00/09184 | * | 2/2000 |
| WO | WO 96/05879 | | 2/1996 |
| WO | WO 96/17648 | * | 6/1996 |
| WO | WO 96/37155 | | 11/1996 |
| WO | WO 96/37256 | | 11/1996 |
| WO | WO 97/03718 | | 2/1997 |
| WO | WO 97/46157 | | 12/1997 |
| WO | WO 97/48440 | | 12/1997 |
| WO | WO 97/48441 | | 12/1997 |
| WO | WO 97/48442 | | 12/1997 |
| WO | WO 98/00193 | | 1/1998 |
| WO | WO 98/11937 | | 3/1998 |

(Continued)

*Primary Examiner*—Catherine S. Williams
(74) *Attorney, Agent, or Firm*—Michael J. Atkins (57) ABSTRACT

A method and device are described for applying a microprotrusion member (44) including a plurality of microprotrusions (90) to the stratum corneum with impact. The method and device are used to improve transport of an agent across the skin for agent delivery or sampling. The applicator (10, 60, 80) causes the microprotrusion member (44) to impact the stratum corneum with a certain amount of impact determined to effectively pierce the skin with the microprotrusions (90). The preferred applicator (10, 60, 80) impacts the stratum corneum with the microprotrusion member (44) with an impact of at least 0.05 joules per cm² of the microprotrusion member (44) in 10 msec or less.

10 Claims, 6 Drawing Sheets

FOREIGN PATENT DOCUMENTS

| WO | WO 98/28037 | * | 7/1998 |
| WO | WO 98/29365 | | 7/1998 |
| WO | WO 99/29298 | | 6/1999 |
| WO | WO9929365 | | 6/1999 |
| WO | WO 99/64580 | | 12/1999 |
| WO | WO 0143643 | | 6/2001 |

* cited by examiner

APPARATUS AND METHOD FOR PIERCING SKIN WITH MICROPROTRUSIONS

TECHNICAL FIELD

The invention relates to an apparatus and method for applying a penetrating member to the stratum corneum by impact, and more particularly, the invention relates to the use of an applicator device providing an impact to reproducibly penetrate the stratum corneum with a microprotrusion array for delivery or sampling of an agent.

BACKGROUND ART

Interest in the percutaneous or transdermal delivery of peptides and proteins to the human body continues to grow as the number of medically useful peptides and proteins becoming increasingly available in large quantities and pure form. The transdermal delivery of peptides and proteins still faces significant problems. In many instances, the rate of delivery or flux of polypeptides through the skin is insufficient, due to their large size and molecular weight, to produce a desired therapeutic effect. In addition, polypeptides and proteins are easily degraded during and after penetration into the skin and prior to reaching target cells. Likewise, the passive transdermal flux of many low molecular weight compounds is too low to be therapeutically effective.

One method of increasing the transdermal delivery of agents relies on utilizing a skin permeation enhancer, either by pretreatment of the skin or co-delivering it with the beneficial agent. A permeation enhancer substance, when applied to a body surface through which the agent is delivered, enhances the transdermal flux of the agent. These enhancers work may function increasing the permselectivity and/or permeability of the body surface, and/or reducing the degradation of the agent.

Another method of increasing the agent flux involves the application of an electric current across the body surface referred to as "electrotransport." "Electrotransport" refers generally to the passage of a beneficial agent, e.g., a drug or drug precursor, through a body surface, such as skin, mucous membranes, nails, and the like. The transport of the agent is induced or enhanced by the application of an electrical potential, which results in the flow of electric current, which delivers or enhances delivery of the agent. Electrotransport delivery generally increases agent delivery and reduces polypeptide degradation during transdermal delivery.

There also have been many attempts to mechanically penetrate or disrupt the skin in order to enhance the transdermal flux, such as, U.S. Pat. No. 5,879,326 issued to Godshall, et al., U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue No. 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365. These devices use piercing elements of various shapes and sizes to pierce the outermost layer (i.e., the stratum corneum) of the skin. The penetrating elements disclosed in these references generally extend perpendicularly from a thin, flat member, such as a pad or sheet. The penetrating elements, often referred to as microblades, are extremely small in some devices. Some of these microblades have dimensions (i.e., a microblade length and width) of only about 25–400 µm and a microblade thickness of only about 5–50 µm. Other penetrating elements are hollow needles having diameters of about 10 µm or less and lengths of about 50–100 µm. These tiny stratum corneum piercing/cutting elements are meant to make correspondingly small microslits/microcuts in the stratum corneum for enhanced transdermal agent delivery, or for enhanced transdermal efflux of a body analyte, therethrough. The perforated skin provides improved flux for sustained agent delivery or sampling through the skin. In many instances, the microslits/microcuts in the stratum corneum have a length of less than 150 µm and a width which is substantially smaller than their length.

When microprotrusion arrays are used to improve delivery or sampling of agents through the skin, consistent, complete, and repeatable penetration of the skin by the microprotrusions is desired. Manual application of a skin patch including microprotrusions often results in significant variation in puncture depth across the microprotrusion array. In addition, manual application results in large variations in puncture depth between applications due to the manner in which the user applies the array. Accordingly, it would be desirable to be able to apply a microprotrusion array to the stratum corneum with an automatic or semi-automatic device which provides microprotrusion skin penetration in a consistent and repeatable manner.

It would be desirable to provide an applicator for consistent and repeatable application of a microprotrusion array to the skin with the applicator applying an impact capable of achieving effective penetration of the stratum corneum with the microprotrusion array.

DISCLOSURE OF THE INVENTION

The present invention relates to a method and device for applying a microprotrusion member including a plurality of microprotrusions to the stratum corneum with impact. Piercing the skin with the microprotrusions is used to improve transport of an agent across the skin. The applicator causes the microprotrusion member to impact the stratum corneum with a certain amount of impact determined to effectively pierce the skin with the microprotrusions. The preferred applicator impacts the stratum corneum with the microprotrusion member with an impact of at least 0.05 joules per $cm^2$ of the microprotrusion member in 10 msec or less.

In accordance with one aspect of the present invention, a method is disclosed for forming a plurality of microslits through the stratum corneum through which an agent can be delivered or sampled. The method involves providing a microprotrusion member having a plurality of stratum corneum-piercing microprotrusions, and causing the microprotrusions to impact the stratum corneum with an impact of at least 0.05 joules per $cm^2$ of the microprotrusion member in 10 msec or less.

Figure 2:
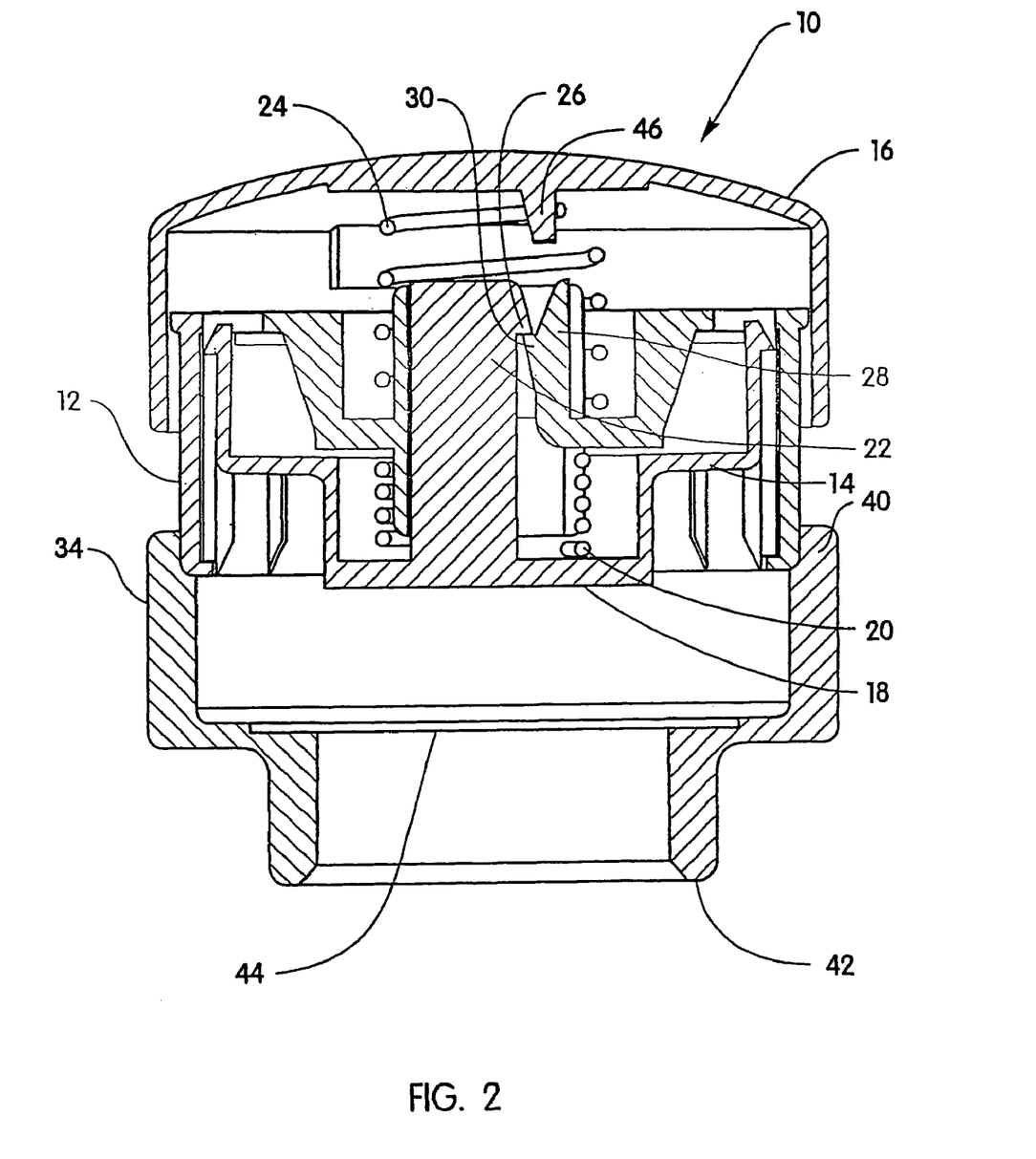
Figure 3:
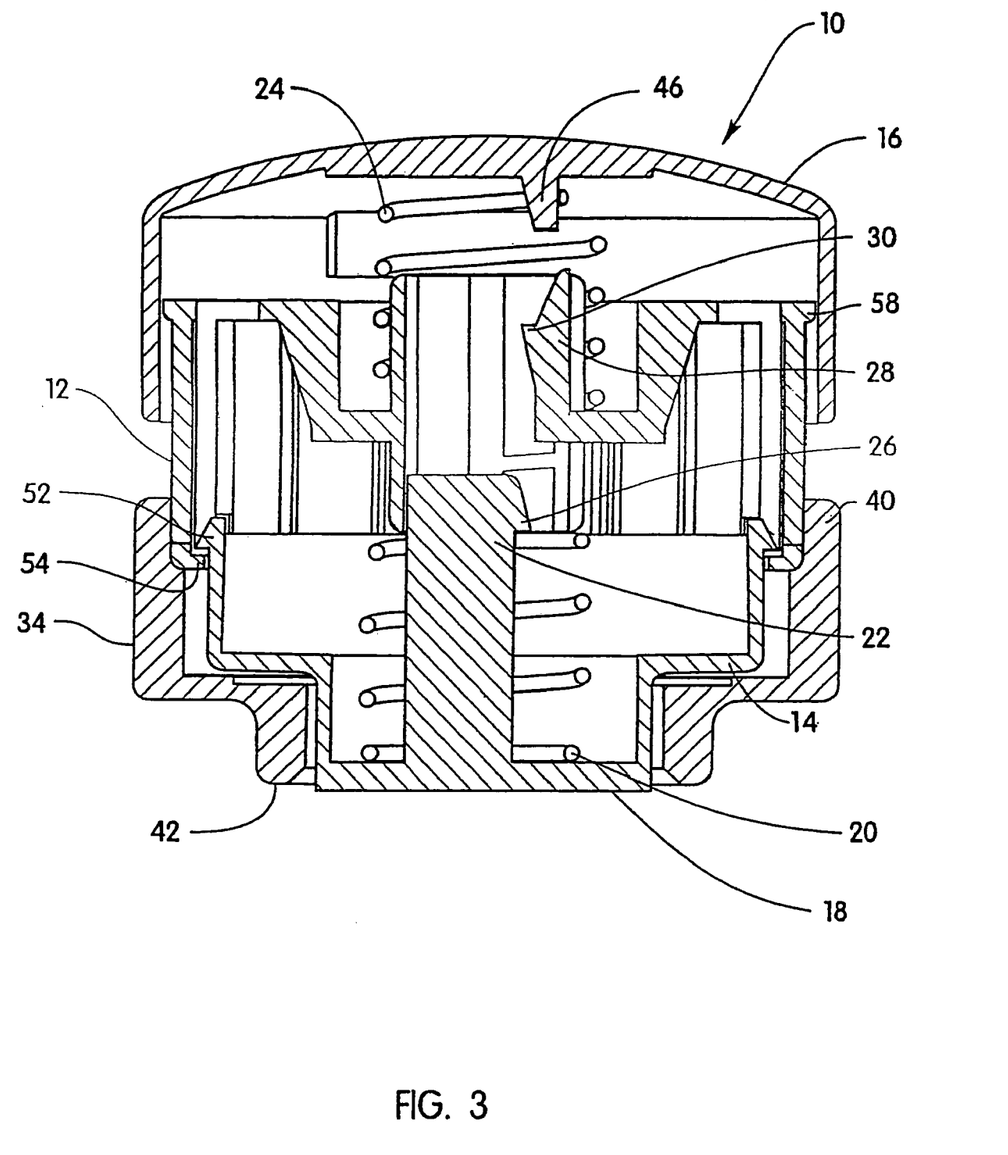

In accordance with another aspect of the present invention, a device is disclosed for forming a plurality of microslits through the stratum corneum through which an agent can be delivered or sampled. The device includes an applicator having a stratum corneum contacting surface, and a microprotrusion member having a plurality of stratum corneum-piercing microprotrusions, the microprotrusion member mounted on the applicator, wherein the applicator, once activated, causes the microprotrusion member to impact the stratum corneum under conditions of at least 0.05 joules per $cm^2$ of microprotrusion member in 10 msec or less.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a side cross sectional view of an applicator device in an initial configuration prior to cocking;

FIG. 2 is a side cross sectional view of the applicator device of FIG. 1 in a cocked position with a patch retainer attached to the applicator;

FIG. 3 is a side cross sectional view of the applicator device of FIG. 1 with the patch retainer of FIG. 2 after the piston has been released to apply the patch;

FIG. 4 is a perspective view of an alternative embodiment of an applicator device;

FIG. 5 is a perspective view of a portion of one example of a microprotrusion array;

FIG. 6 is a side sectional view of a pressure driven applicator device; and

FIG. 7 is a graph of dose M (in μg) of ovalbumin delivered over two time periods (5 seconds and 1 hour) from dry coated microprotrusions arrays applied using manual finger pressure (non-hatched bars) and using automatic applicators in accordance with the present invention (hatched bars).

MODES FOR CARRYING OUT THE INVENTION

FIG. 1 illustrates an applicator device 10 for repeatable impact application of an array of microprotrusions to the stratum corneum. The applicator device 10 is configured to achieve a predefined and consistent impact of a microprotrusion member including an array of microprotrusions on the stratum corneum to provide acceptable penetration of the stratum corneum with the microprotrusions. In particular, the applicator device 10 has been designed to optimize the power per unit area of the impact to achieve effective penetration of the stratum corneum with the microprotrusions.

As will be described in further detail below, it has been determined that the applicator device 10 should deliver range of power per unit area of a microprotrusion member for effective penetration of the stratum corneum. The range of power per unit area is represented as a minimum energy per unit area delivered to the skin site in a maximum amount of time.

One embodiment of the applicator device 10, as shown in FIGS. 1–3, includes a device body 12 and a piston 14 movable within the device body. A cap 16 is provided on the device body 12 for activating the applicator to impact the stratum corneum with a microprotrusion member (not shown in FIG. 1). An impact spring 20 is positioned around a post 22 of the piston 14 and biases the piston downward with respect to the device body 12. The piston 14 has a lower surface 18 which is substantially planar or configured to a bodily surface. Upon activation of the applicator device the impact spring 20 moves the piston 14 and causes a microprotrusion member, such as a transdermal patch containing a microprotrusion array to impact and pierce the stratum corneum.

FIG. 1 shows the piston 14 in an uncocked position, while FIG. 2 shows the piston in the cocked position. When the applicator device is cocked, the piston 14 is pressed up inside the device body 12 and locked in place by a locking mechanism. The locking mechanism includes a catch 26 on the post 22 and a flexible finger 28 on the device body 12 having a corresponding latch 30. As the piston 14 is moved toward the device body 12 compressing the impact spring 20, the catch 26 flexes the finger 28 and snaps over the corresponding latch 30 of the flexible finger. The cocking step may be performed by a single compression motion which both cocks and locks the piston 14 in the cocked position.

FIG. 2 illustrates the applicator device 10 with the piston 14 in a cocked configuration. As shown in FIG. 2, with the device in the cocked position, the catch 26 and latch 30 on the piston 14 and device body 12 are releasably engaged preventing downward motion of the piston in the device body.

FIG. 2 also illustrates a retainer ring 34 mounted on the device body 12. The retainer ring 34 has a first end 40 which is configured to friction fit onto the device body 12. A second end 42 of the retainer ring 34 provides a stratum corneum contacting surface. A microprotrusion member 44 including the microprotrusions is mounted between the first and second ends 40, 42 of the retainer ring 34. The microprotrusion member 44 is suspended in the retainer ring 34. The manner in which the microprotrusion member 44 is mounted in the retainer ring 34 and the location of the microprotrusion member may vary. For example, the microprotrusion member 44 may be positioned adjacent the second end 42 of the retainer ring 34.

According to one example, the microprotrusion member 44 is connected by frangible sections of base material to an annular ring of base material which is adhered to the retainer ring 34. When the piston 14 of applicator device 10 is released, the microprotrusion member 44 is separated from the retainer ring 34 by the downward force of the piston 14. Alternatively, the microprotrusion member 44 may be releasably attached to the piston 14 or positioned on the skin beneath the piston.

The retainer ring 34 is attached to the device body 12 after cocking of the piston 14. The retainer ring 34 is attached by a snap in connection, a bayonet fitting, or a slide on fitting which allows the retainer ring 34 to slide on the device body 12 in a direction normal to the axis of the applicator.

The applicator device 10 has been described for use with a microprotrusion member 44, such as a transdermal patch. A transdermal patch useful with the present invention generally includes a microprotrusion array, an agent reservoir, and a backing. However, the applicator device 10 may also be used with a microprotrusion member without an agent reservoir. In this case, the microprotrusion member is used as a pretreatment which is followed by the application or sampling of an agent with a separate device. Alternatively, the microprotrusion member may incorporate the agent as a coating on the microprotrusions, e.g. for delivering a vaccine intradermally.

The activation of the applicator device 10 by releasing the locking mechanism is performed by downward force applied to the applicator cap 16 while the second end 42 of the retainer ring 34 is held against the skin with a hold down force. The cap 16 is biased upwards by a hold down spring 24 which is positioned between the device body 12 and the cap. The cap 16 includes a pin 46 extending downward from the cap. When the cap 16 is pressed downward against the bias of the hold down spring 24, the pin 46 contacts a ramp 48 on the flexible finger 28 moving the flexible finger outward and disengaging the latch 30 of the flexible finger from the catch 26. When the predetermined hold down force is achieved, the piston 14 is released and moves downward impacting the stratum corneum with the microprotrusion member 44. FIG. 3 illustrates the applicator device 10 after the device has been activated and a microprotrusion member has been impacted against the stratum corneum.

Figure 1:
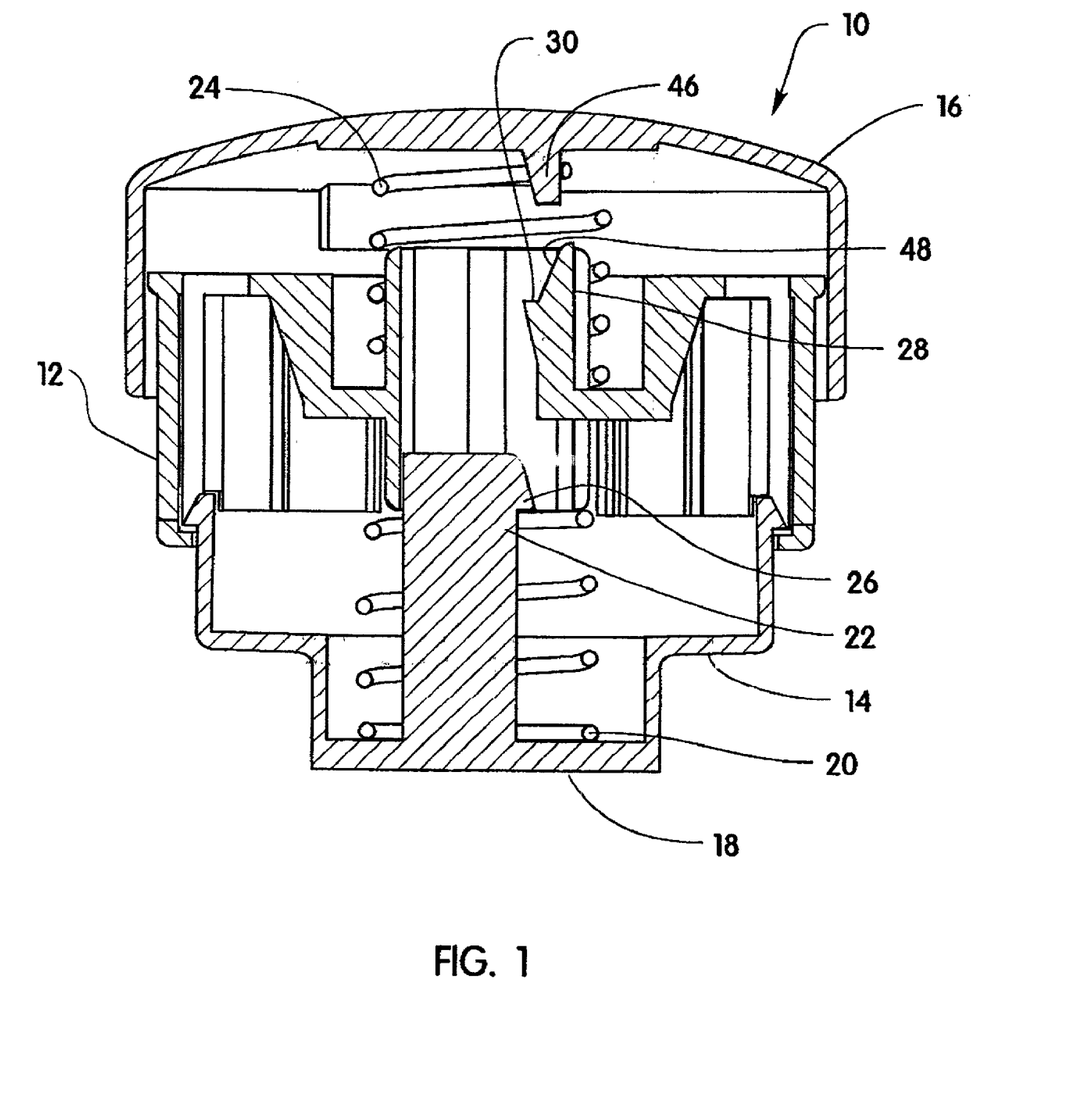

The hold down spring 24 is selected such that a predetermined hold down force must be achieved before the applicator device 10 is activated. The hold down force causes the stratum corneum to be stretched by the surface 42 of the retainer ring 34 so that the skin is under optimal tension at the time the microprotrusion member 44 impacts the skin.

The hold down force applied by the hold down spring 24 is preferably selected to cause the second end 42 of the retainer ring 34 to apply a tension to the skin in the range of about 0.01 to 10 megapascals (MPa), more preferably about 0.05 to 2 MPa. The hold down force with which the skin contacting surface 42 of the retainer ring 34 is held against the skin when the piston 14 is released, is preferably at least 0.5 kg, and more preferably, at least 1.0 kg.

A balance between the hold down spring 24 and the impact spring 20 allows the cocking of the piston 14 by pressing on the cap 16 without causing the finger 46 to release the locking mechanism. In other words, upon application of a cocking force to the applicator device 10, the impact spring 20 will be deflected prior to the deflection of the hold down spring 24.

The impact spring 20 is selected to apply a force to the piston which achieves a predetermined impact of the microprotrusion member 44 against the stratum corneum. The microprotrusion member 44 is impacted with an energy which provides a desired skin penetration with the microprotrusions. The impact spring 20 is also preferably selected to achieve the desired skin penetration without exceeding an impact which causes discomfort to the patient.

The impact of the microprotrusion member against the stratum corneum is determined by the following features of the applicator device: 1) the distance (x) the piston 14 travels from the cocked and locked position (shown in FIG. 2) to the skin; 2) the amount of compression in the impact spring 20 when the piston 14 is in the cocked and locked position; 3) the rate (k) of the impact spring 20 as it moves from the cocked and locked position to the skin impacting position; 4) the time (t) in which the potential energy (PE) of the impact spring 20 is imparted as kinetic energy (KE) to the skin; 5) the mass (m) of the moving impact piston and patch with the microprotrusion array; 6) any energy loss (L) associate with friction or breakage of the frangible connections holding the patch on the retainer; and 7) the area (A) of impact. The impact is also effected by conditions external to the applicator device including the configuration of the microprotrusion member and the condition of the skin (e.g., stretched or unstretched) on impact. These conditions external to the applicator device have been taken into account in determining the desired impact power.

The power of impact (P) per unit area (A) of the microprotrusion array is defined as follows:

$$P/A=(KE)/(A)(t)$$

wherein: $PE=KE+L$ $$PE=0.5(k)(x)^2$$

$$KE=0.5(m)(v)^2$$

$$P=(KE)/(t)$$

$$P/A=(KE)/(A)(t)$$

EXAMPLES

The following are examples of applicator systems having impact springs which provide acceptable power per unit area for delivery of a microprotrusion member, as tested on human skin. The applicator 10 described earlier herein was configured with three different impact springs having different spring constants and lengths as shown below. These three applicator/spring configurations where found to be acceptable for delivery of microblade arrays having the three different areas listed below. The microprotrusion device delivered was substantially similar to the device illustrated in FIG. 5 having microblades with lengths of about 250 μm.

| Microblade array area | Spring | spring constant (K) | spring length (L) | Total Energy Delivered | Energy/Area |
|---|---|---|---|---|---|
| 1 cm² | #71512 | 9.3 lb/in | 1.75 in | 0.36 J | 0.36 J/cm² |
| 2 cm² | #71526 | 14 lb/in | 1.75 in | 0.63 J | 0.32 J/cm² |
| 3.3 cm² | #71527 | 12 lb/in | 2.00 in | 1.07 J | 0.32 J/cm² |

The impact spring 20 is preferably selected to deliver a minimum amount of energy of 0.05 Joules per cm², which is delivered in less than 10 milliseconds (msec). A preferred amount of energy is a minimum of 0.10 Joules per cm², which is delivered in less than 1 msec. A maximum amount of energy delivered by the impact spring 20 is about 0.3 Joules per cm². The maximum amount of energy delivered has been determined based on the balance between the use of additional energy to achieve additional blade penetration and a desire to prevent discomfort (e.g. pain and bruising) caused by impacting the stratum corneum with the microprotrusion member.

Figure 4:
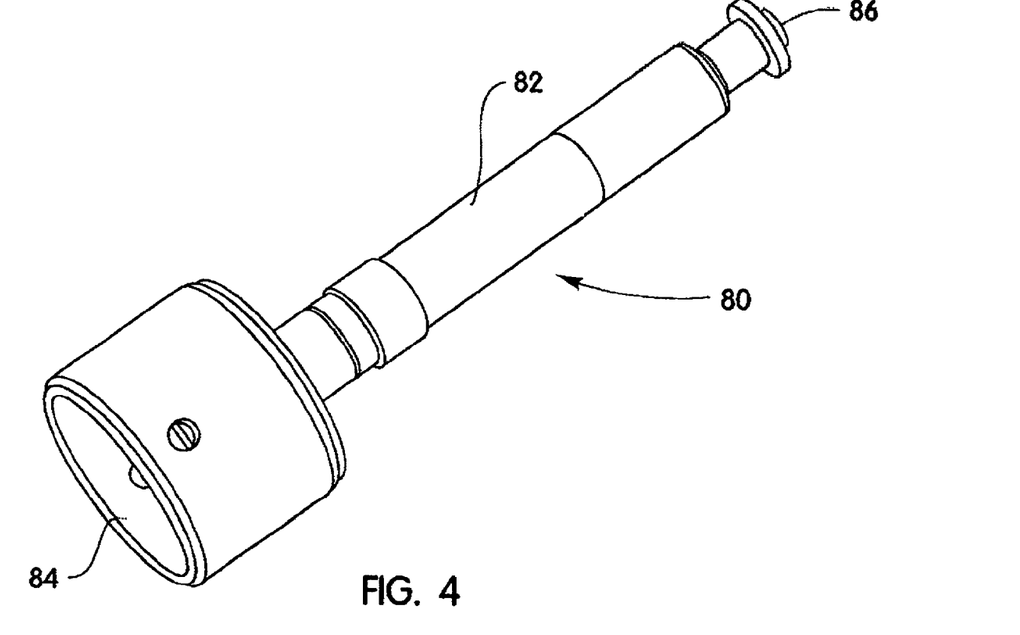

FIG. 4 illustrates an alternative embodiment of an applicator 80 having a different shape and a release button 86 for manual activation. According to this embodiment, a user grasps a handle 82 of the applicator device 80 and presses a lower end 84 of the device against the stratum corneum. Activation of the applicator device 80 is performed manually by pressing the release button 86 and the amount of hold down force is controlled manually and independently of the when the release button 86 is pressed. The applicator 80 of FIG. 4 may include a hold down indicator on the applicator handle 82 which indicates to the user (e.g., by means of an audible, tactile, or visible signal) when the predetermined hold down force has been achieved and the release button 86 should be pressed.

The applicator devices 10, 80 according to the present invention have been described with respect to an upright orientation in which the microprotrusion member 44 is applied from a piston side of the device which is illustrated at the bottom of the devices in the figures. It should be understood that the applicator devices may be used in other orientations.

While the applicator devices 10 and 80 are spring-loaded, it will be appreciated by those skilled in the art that other known energy sources (e.g., pressure, electricity, magnets and other biasing members besides compression springs such as tension/extension springs and rubber bands) can be used in place of the spring 20 and are considered equivalents thereof as long as such alternative energy source provides the prescribed minimum power at impact.

Figure 6:
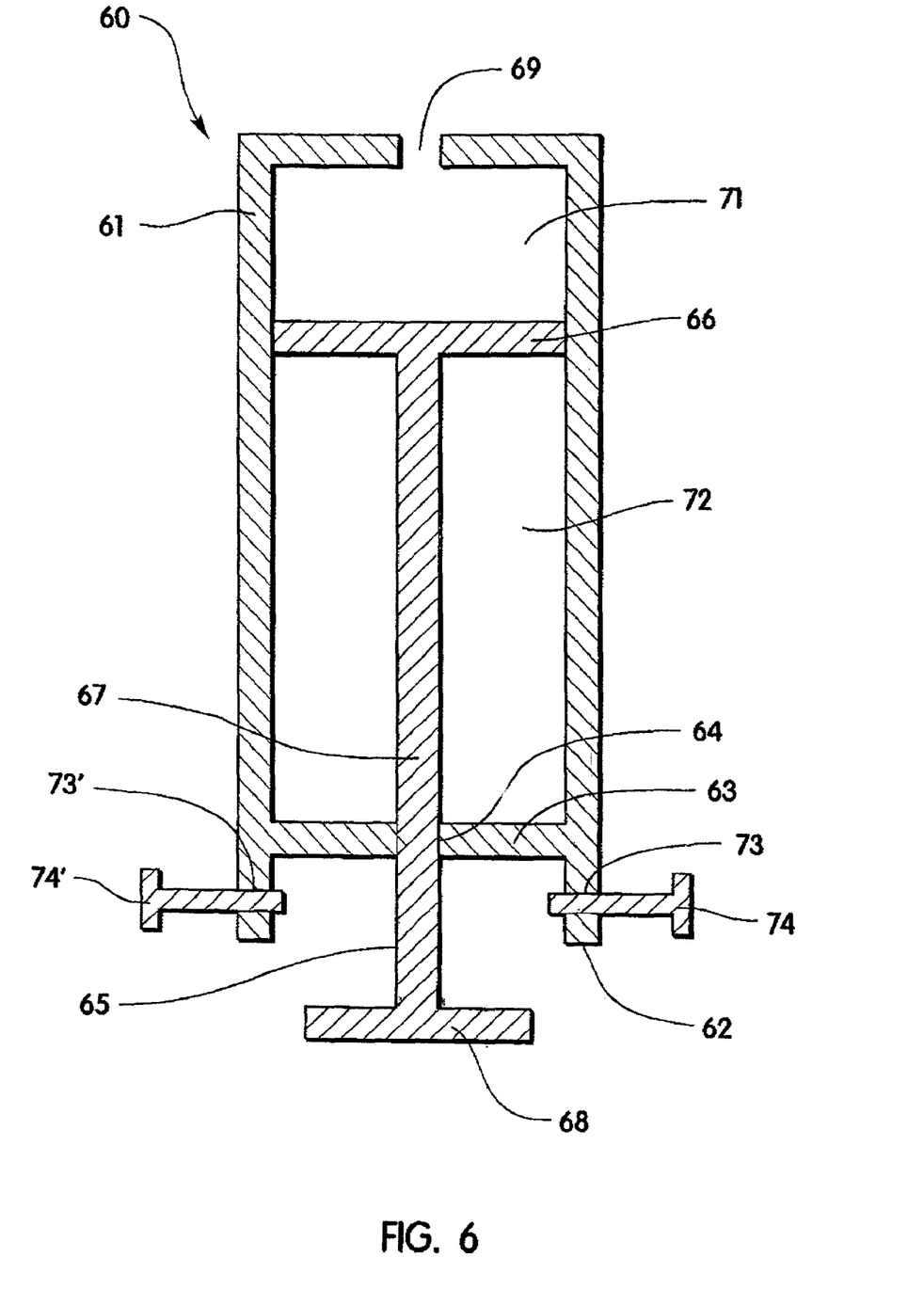

One example of a pressure driven applicator device is shown in FIG. 6. Pressure driven applicator 60 has a tubular body 61 with a recessed cap 63. The recessed cap has a central orifice 64 through which is disposed rod 67 of piston rod unit 65. At the upper end of rod 67 is disposed a piston 66 which slidingly and sealingly engages the inner surface of body 61. As can be seen, the piston 66 also divides the interior space within body 61 into an upper chamber 71 and a lower chamber 72. Rod 67 also slidingly and sealingly engages the central orifice 64 in recessed cap 63. Disposed on the lower end of rod 67 is an impact head 68 which is adapted to impact the skin-piercing microprotrusion member described elsewhere herein against the patient's skin. To operate the applicator 60, the piston 66 is moved from a position adjacent recessed cap 63 and slid upwardly towards orifice 69 by pressing on impact head 68. As piston 66 moves upwardly within the interior of body 61, air within chamber 71 is expelled through orifice 69. Further, because of the sealing contact of the piston 66 with the inside surface of body 61 and the sealing contact of the rod 67 with orifice 64, a partial vacuum is formed within chamber 72. When impact head 68 engages the lower surface of recessed cap 63, a sliding catch 74 is pressed through opening 73 in body 61. Optionally, a second sliding catch 74' is disposed in opening 73'. Thus, the sliding catches 74 and 74' act to hold the impact head 68 against cap 63 against the force exerted by the partial vacuum within chamber 72. Once secured by sliding catches 74 and 74', the microprotrusion member can be mounted on the lower surface of impact head 68. Once this is done, the applicator 60 is placed against the patient's skin with edge 62 contacting the skin. The sliding catch 74 is then pulled out causing the impact head 68 to impact the mounted microprotrusion member against the skin, causing the microprotrusions to pierce the skin.

Optionally, the orifice 69 may be eliminated. In such a configuration, the piston rod unit 65 is driven not only by a partial vacuum formed within chamber 72 but also a positive (i.e., above atmospheric) pressure within chamber 71.

Figure 5:
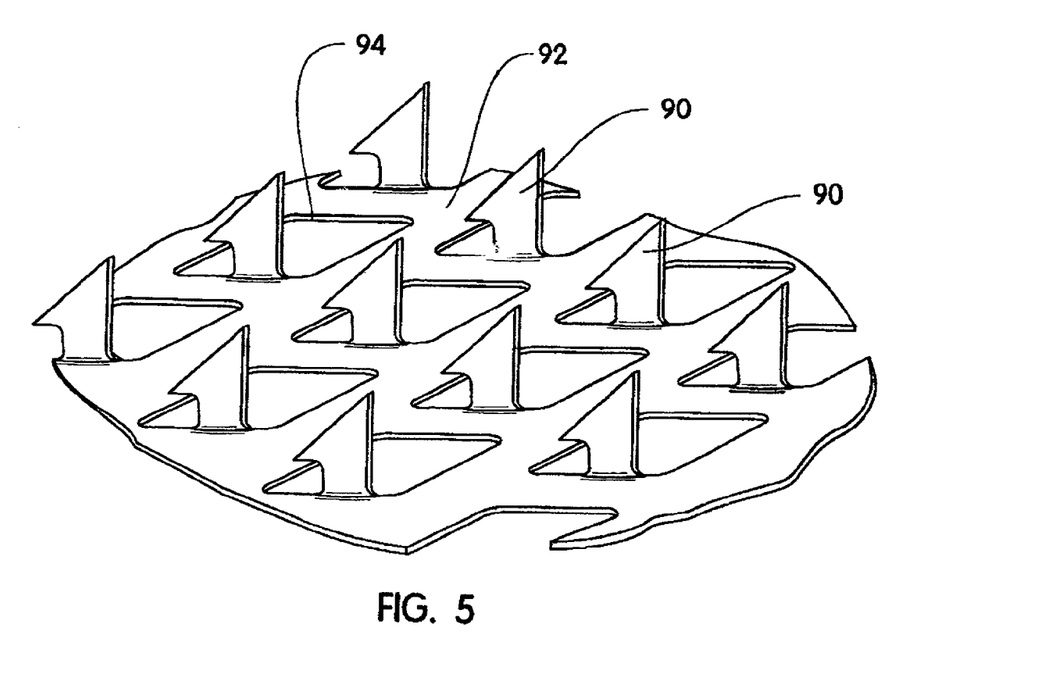

FIG. 5 illustrates a portion of one embodiment of a microprotrusion member for piercing the stratum corneum for use with the present invention. FIG. 5 shows a plurality of microprotrusions in the form of microblades 90. The microblades 90 extend at a substantially 90° angle from a sheet 92 having openings 94. The sheet 92 may be incorporated in an agent delivery patch or an agent sampling patch which includes an agent reservoir and an adhesive for adhering the patch to the stratum corneum. Examples of agent delivery and sampling patches which incorporate a microprotrusion array are found in WO 97/48440, WO 97/48441, WO 97/48442. The microprotrusion array of FIG. 5 without a reservoir may also be applied alone as a skin pretreatment.

The term "microprotrusion" as used herein refers to very tiny stratum corneum piercing elements typically having a length of less than 500 μm, and preferably less than 250 μm, which make a penetration in the stratum corneum. In order to penetrate the stratum corneum, the microprotrusions preferably have a length of at least 10 μm, more preferably at least 50 μm. The microprotrusions may be formed in different shapes, such as needles, hollow needles, blades, pins, punches, and combinations thereof.

The term "microprotrusion member" as used herein refers to a member including a plurality of microprotrusions for piercing the stratum corneum. The microprotrusion member may be formed by cutting a plurality of blades from a thin sheet and folding each of the blades out of the plane of the sheet to form the configuration shown in FIG. 5. The microprotrusion member may also be formed in other known manners, such as by connecting multiple strips having microprotrusions along an edge of each of the strips as disclosed in Zuck WO 99/29364 which is incorporated herein by reference. The microprotrusion member may include hollow needles which inject a liquid formulation.

Examples of microprotrusion arrays are described in U.S. Pat. No. 5,879,326 issued to Godshall, et al., U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365, all of which are incorporated herein by reference in their entirety.

The device of the present invention can be used in connection with agent delivery, agent sampling, or both. In particular, the device of the present invention is used in connection with transdermal drug delivery, transdermal analyte sampling, or both. Examples of agents which may be delivered include drugs and vaccines. An example of a body analyte which may be sampled is glucose. Transdermal delivery devices for use with the present invention include, but are not limited to passive devices, osmotic devices, pressure-driven devices, and electrotransport devices. Transdermal sampling devices for use with the present invention include, but are not limited to, passive devices, negative pressure driven devices, osmotic devices, and reverse electrotransport devices. The transdermal devices of the present invention may be used in combination with other methods of increasing agent flux, such as skin permeation enhancers.

The device of the present invention may be used with a microprotrusion member, such as a transdermal delivery or sampling patch having adhesive for attaching the patch to the skin. Alternatively, the microprotrusion member and a delivery or sampling patch may be two separate elements with the microprotrusion member used for pretreatment prior to application of the delivery or sampling patch.

Example 1

Titanium microprotrusion embers comprising a circularsheet (sheet area was 2 $cm^2$) having microprotrusions with the shape and configuration shown in FIG. 5 (microprotrusion length of 360 μm, and a microprotrusion density of 190 microprotrusions/$cm^2$) were coated with the model protein vaccine ovalbumin. A 200 mg/mL aqueous coating solution of fluorescein-tagged ovalbumin was prepared. For coating, the microprotrusion members were immersed briefly in this solution, blown dry, and allowed to dry overnight at room temperature. Subsequent analysis demonstrated that the microprotrusion members were coated with ovalbumin at 200 to 250 μg/$cm^2$.

A study was performed in hairless guinea pigs (HGPs) to evaluate ovalbumin absorption into the skin after short (5 second) application of the microprotrusion members. The system applied comprised a coated microprotrusion member adhered to the center of a low density polyethylene (LDPE) backing with the acrylate adhesive (8 cm² disc). In one group of five HGPs, the systems were applied with an impact applicator. The impact applicator impacted the system against the animals' skin with an impact energy of 0.42 J in less than 10 m sec and the system was removed after 5 seconds contact with the skin. In a second group of five HGPs, the system was applied to the skin using a 2 kg/cm² manual pressure, held in place for 5 seconds, then removed. In both groups, penetration was similar as evidenced by good retention of the microprotrusions into the skin. Following removal of the system, residual drug was thoroughly washed from the skin and a 8 mm skin biopsy was taken at the location of the microprotrusion member application. The total amount of ovalbumin delivered into the skin was determined by dissolving the skin biopsy sample in hyamine hydroxide (diisobutylcresoxyethoxyethyl) (dimethyl) benzylammonium hydroxyde, 1 M in ethanol, sold by J. T. Baker (NJ, USA) and quantitation performed by fluorimetry. Results showed that impact application resulted in an average delivery of 30.1 μg ovalbumin while only 6.6 μg of ovalbumin was delivered on average with manual application.

Example 2

A second experiment was performed with dry-coated ovalumin to compare delivery following impact and manual application using a different titanium microprotrusion member and a longer application time. A 200 mg/mL aqueous coating solution of fluorescein-tagged ovalbumin was prepared. The microprotrusion members (microprojection length 214 μm, no retention feature, 292 microprojections/cm², 2 cm² disc) were immersed briefly in the coating solution, blown dry and allowed to dry overnight at room temperature. Subsequent analysis demonstrated that the microprotrusion members were coated with ovalbumin at 200 to 250 μg/cm².

Figure 7:
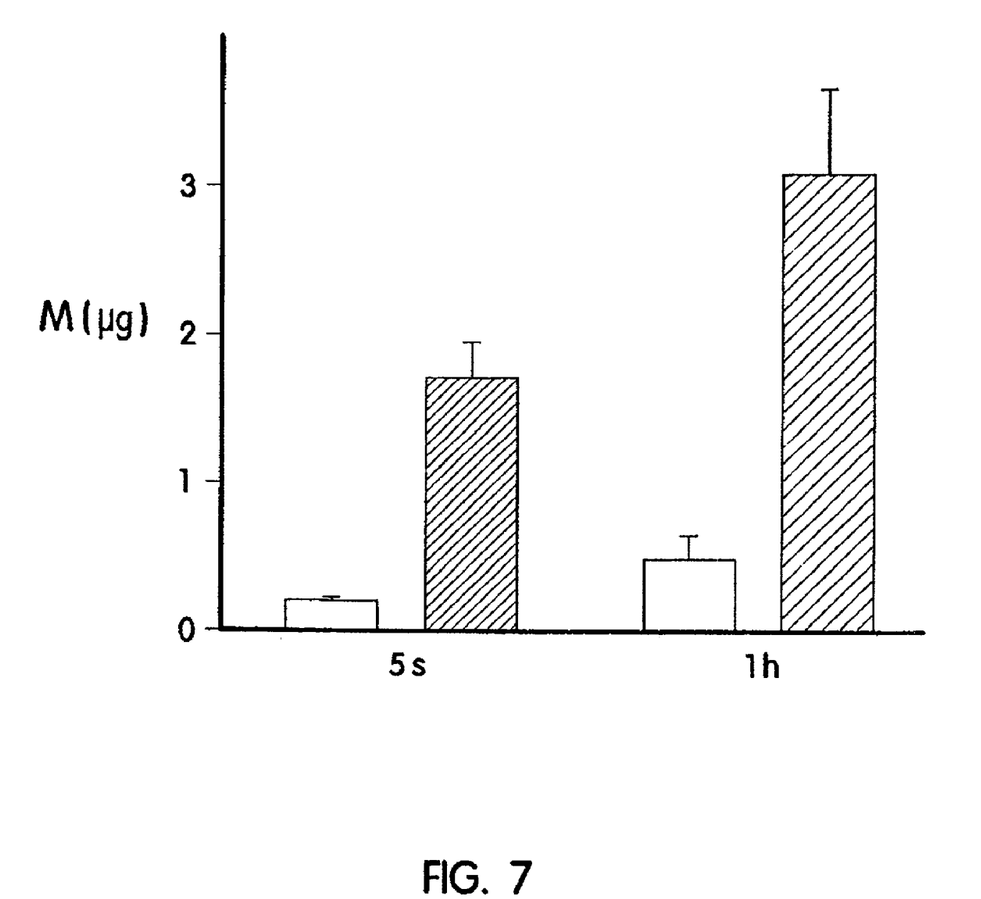

The delivery study was performed in hairless guinea pigs (HGPs). The system applied comprised a coated microprotrusion members adhered to the center of a LDPE backing with acrylate adhesive (8 cm² disc). In one group of five HGPs, microprotrusion member application was performed with an impact applicator (0.2 J/cm² in less than 10 msec) and the system was removed after 5 seconds contact with the skin. In a second group of five HGPs, the system was applied to the skin using a 2 kg/cm² manual pressure, held in place for 5 seconds, then removed. Two additional groups of hairless guinea pigs were treated as described above except that, following application, the system was left in contact with the skin for 1 hour. Following removal of the system, residual drug was thoroughly washed from the skin and a 8 mm skin biopsy was taken at the location of the microprotrusion member application. The total amount of ovalbumin delivered into the skin was determined by dissolving the skin biopsy sample in hyamine hydroxide and quantitation performed by fluorimetry. The results of amount of ovalbumin delivered (M) for the two time periods (t) are presented in FIG. 7 and demonstrate that higher delivery following impact application as compared to manual application is independent of the application time.

Examples 1 and 2 demonstrate that the higher amounts of ovalbumin delivered using impact application, as compared with manual application9on, is independent of the microprotrusion members design, the type of coating and the application time.

While the invention has been described in detail with reference to the preferred embodiments thereof, it will be apparent to one skilled in the art that various changes and modifications can be made and equivalents employed, without departing from the present invention.

What is claimed is:

1. A method of transferring an agent through the stratum corneum of a subject, comprising the steps of:
    providing a microprotrusion member having one or more stratum corneum-piercing microprotrusions;
    placing said microprotrusion member proximate a skin site on the subject;
    striking said microprotrusion member with an impact force, whereby said microprotrusion member imparts an energy on impact with the stratum corneum in the range of approximately 0.05–3 joules per cm² of said microprotrusion member in no greater than 10 milliseconds, and whereby at least one of said stratum corneum-piercing microprotrusions forms a microslit through the stratum corneum of the subject; and
    transferring the agent through said microslit.

2. The method of claim 1, wherein said stratum corneum-piercing microprotrusions have a length less than 500 μm.

3. The method of claim 1, wherein said agent is selected from the group consisting of a drug, vaccine, glucose and body analyte.

4. A method of transferring an agent through the stratum corneum of a subject, comprising the steps of:
    providing a microprotrusion member having one or more stratum corneum-piercing microprotrusions;
    striking said microprotrusion member with an impact force, whereby said microprotrusion member imparts an energy on impact with the stratum corneum in the range of approximately 0.1–0.3 joules per cm² of said microprotrusion member in the range of 1–10 milliseconds, and whereby at least one of said stratum corneum-piercing microprotrusions forms a microslit through the stratum corneum of the subject; and
    transferring the agent through said microslit.

5. The method of claim 4, wherein said stratum corneum-piercing microprotrusions have a length less than 500 μm.

6. The method of claim 4, wherein said agent is selected from the group consisting of a drug, vaccine, glucose and body analyte.

7. A method of transferring an agent through the stratum corneum of a subject, comprising the steps of:
    providing a microprotrusion member having one or more stratum corneum-piercing microprotrusions;
    providing an impact applicator adapted to provide a first impact force;
    placing said microprotrusion member proximate a skin site on the subject;
    placing said impact applicator proximate said skin site in operational relationship with said microprotrusion member;
    actuating said impact applicator to impart said first impact force to said microprotrusion member, whereby said microprotrusion member imparts an energy on impact with the stratum corneum in the range of 0.1–0.3 joules per cm² of said microprotrusion member in a first period of time in the range of 1–10 milliseconds, and whereby at least one of said stratum corneum-piercing microprotrusions forms a microslit through the stratum corneum of the subject; and transferring the agent through said microslit.

8. The method of claim 7, wherein said step of placing said impact applicator proximate said skin site comprises applying a hold down force to said skin site in the range of approximately 0.5–1 kg.

9. The method of claim 7, wherein said stratum corneum-piercing microprotrusions have a length less than 500 µm.

10. The method of claim 7, wherein said agent is selected from the group consisting of a drug, vaccine, glucose and body analyte.

* * * * *